United States Patent
Foxall et al.

(10) Patent No.: US 10,203,395 B2
(45) Date of Patent: Feb. 12, 2019

(54) QUALITY ASSURANCE APPARATUS AND METHOD FOR MAGNETIC RESONANCE BASED RADIATION THERAPY PLANNING

(71) Applicant: KONINKLIJKE PHILIPS N.V., Eindhoven (NL)

(72) Inventors: David Leslie Foxall, Highland Heights, OH (US); Melanie Suzanne Kotys, Highland Heights, OH (US); Ajit Devaraj, Highland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 666 days.

(21) Appl. No.: 14/386,134

(22) PCT Filed: Mar. 22, 2013

(86) PCT No.: PCT/IB2013/052292
§ 371 (c)(1),
(2) Date: Sep. 18, 2014

(87) PCT Pub. No.: WO2013/144802
PCT Pub. Date: Oct. 3, 2013

(65) Prior Publication Data
US 2015/0088449 A1    Mar. 26, 2015

Related U.S. Application Data

(60) Provisional application No. 61/616,548, filed on Mar. 28, 2012.

(51) Int. Cl.
*G01R 33/58* (2006.01)
*G01R 33/30* (2006.01)
(Continued)

(52) U.S. Cl.
CPC .......... *G01R 33/583* (2013.01); *A61B 5/0035* (2013.01); *A61B 5/055* (2013.01);
(Continued)

(58) Field of Classification Search
CPC .......... A61B 2560/0228; A61B 5/0035; A61B 5/055; A61B 6/032; A61B 6/583;
(Continued)

(56) References Cited

U.S. PATENT DOCUMENTS 6,842,502 B2 *  1/2005  Jaffray ................... A61B 6/032
                                                  378/19
7,056,019 B1    6/2006  Hanson
(Continued)

FOREIGN PATENT DOCUMENTS

JP    2011239830 A    12/2011
RU    2171652 C2       8/2001

OTHER PUBLICATIONS

Wang et al, "Geometric Distortion in Structural Magnetic Resonance Imaging" Current Medical Imaging Reviews, 2005, P. 49-60.
(Continued)

*Primary Examiner* — John H Le (57) ABSTRACT

A system (20) for quality assurance of a magnetic resonance (MR) imaging device (23) used in magnetic resonance based radiation therapy planning includes a phantom (10) weighing less than 18.2 kg (40 lbs.). The phantom includes a three dimensional spatial distribution of MR and CT imagable elements (12) located in an MR and CT inert foam support (14), and an MR and CT inert external support structure (16) which surrounds and hermetically seals the foam support. The spatial distribution is sized to completely fill an imaging volume of the magnetic resonance imaging device.

18 Claims, 6 Drawing Sheets

(51) Int. Cl.
| | |
|---|---|
| A61B 6/00 | (2006.01) |
| A61B 5/00 | (2006.01) |
| A61B 6/03 | (2006.01) |
| A61B 5/055 | (2006.01) |
| G01R 33/46 | (2006.01) |
| G01R 33/48 | (2006.01) |
| A61N 5/10 | (2006.01) |

(52) U.S. Cl.
CPC ............. *A61B 6/032* (2013.01); *A61B 6/583* (2013.01); *A61N 5/1039* (2013.01); *G01R 33/30* (2013.01); *G01R 33/46* (2013.01); *G01R 33/4812* (2013.01); *G01R 33/58* (2013.01); *A61B 2560/0228* (2013.01); *A61N 2005/1076* (2013.01)

(58) Field of Classification Search
CPC .......... A61N 2005/1076; A61N 5/1039; G01R 33/30; G01R 33/46; G01R 33/4812; G01R 33/58; G01R 33/583
USPC .... 702/104, 152, 153, 155, 172; 378/18, 62, 378/65; 600/439, 416, 437, 407; 324/318; 382/131, 287
See application file for complete search history.

(56) References Cited

U.S. PATENT DOCUMENTS

| | | | |
|---|---|---|---|
| 7,256,392 B2 | 8/2007 | Sendai | |
| 7,330,026 B2 | 2/2008 | Wang | |
| 7,755,031 B2 | 7/2010 | Jang | |
| 7,782,054 B2 | 8/2010 | Werthner | |
| 2003/0212320 A1 | 11/2003 | Wilk | |
| 2005/0013406 A1* | 1/2005 | Dyk | A61N 5/1049 378/65 |
| 2006/0036170 A1 | 2/2006 | Lachaine et al. | |
| 2006/0195030 A1 | 8/2006 | Ogrezeanu et al. | |
| 2008/0085041 A1 | 4/2008 | Breeuwer | |
| 2009/0226066 A1 | 9/2009 | Williams | |
| 2010/0021029 A1 | 1/2010 | Pearlstein | |
| 2010/0066372 A1 | 3/2010 | Breuer | |
| 2010/0288916 A1* | 11/2010 | Cho | A61N 5/1071 250/252.1 |
| 2011/0229055 A1 | 9/2011 | Clarke | |

OTHER PUBLICATIONS

Wang et al, "A Novel Phantom and Method for Comprehensive 3-Dimensional Measurement and Correction of Geometric Distortion in Magnetic Resonance Imaging" Magnetic Resonance Imaging 22 (2004) P. 529-542.

Wang et al, "Geometric Distortion in Clinical MRI Systems Part I: Evaluation Using a 3D Phantom" Magnetic Resonance Imaging 22 (2004) P. 1211-1221.

Wang et al, "Geometric Distortion in Clinical MRI Systems Part II: Correction Using a 3D Phantom" Magnetic Resonance Imaging 22 (2004) P. 1223-1232.

Serge Langlois, Michel Desvignes, Jean-Marc Constans, Marinette Revenu. MRI geometric distorsion: A simple approach to correcting the effects of non-linear gradient fields. Journal of Magnetic Resonance Imaging, Wiley-Blackwell, 1999, 9, pp. 821-831.

Sumanaweera, T., Glover, G., Song, S., Adler, J. and Napel, S. (1994), Quantifying MRI geometric distortion in tissue. Magn. Reson. Med., 31: 40-47. doi:10.1002/mrm.1910310106.

Lee et al "Software Based Algorithm for Modeling and Correction of Gradient Nonlinearity Distortions in Magnetic Resonance Imaging" Advances in Electrical and Electronics Engineering 2008.

* cited by examiner

QUALITY ASSURANCE APPARATUS AND METHOD FOR MAGNETIC RESONANCE BASED RADIATION THERAPY PLANNING

CROSS-REFERENCE TO PRIOR APPLICATIONS

This application is the U.S. National Phase application under 35 U.S.C. §371 of International Application No. PCT/IB2013/052292, filed on Mar. 22, 2013, which claims the benefit of U.S. Provisional Patent Application No. 61/616,548, filed on Mar. 28, 2012. These applications are hereby incorporated by reference herein.

The following relates generally to medical imaging and therapy planning using magnetic resonance imaging. It finds particular application in conjunction with quality assurance of magnetic resonance imaging and medical phantoms, and will be described with particular reference thereto. However, it will be understood that it also finds application in other usage scenarios and is not necessarily limited to the aforementioned application.

Radiation therapy (RT), brachytherapy and pre-surgical planning involves the use of medical images to determine the best procedure to destroy cancerous tumors. In RT, high energy beams are planned to intersect a target, e.g. a tumor, from multiple angles such that the cumulative radiation dose at the tumor is sufficient to kill the tumor tissue, but the dose from any one angle or beam path is below the threshold so as not to kill non-tumor tissue along the path. High energy beam systems used in RT are either gamma ray systems (e.g. Gamma Knife), electron beam systems (e.g. LINAC), charged particle therapy systems, a proton therapy systems, X-ray therapy systems or external beam radiation systems. In brachytherapy systems, radioactive devices are implanted in the body at the site of the tumor to locally deliver treatment. In surgery, a plan is developed to resect the tumor in the least invasive way. In order to plan for these therapies spatially accurate images are needed. Computed Tomography (CT) images are often used, because CT images are geometrically accurate. However, CT involves the use of x-rays, while magnetic resonance (MR) does not employ x-rays. MR also discriminates soft tissue better than CT. Radiation Therapy also includes the evaluation of radiation treatments with the changes that occur in the tissues at the target site. For example, vital tumor tissue, edema tissue, and necrotic tissue are evaluated differently. However, the magnetic fields and gradients tend to have geometric non-linearities or distortions, particularly towards the periphery of the imaging region. As long as these non-linearities or distortions are accurately mapped to the periphery, resultant images are linear and accurate, even at the edges.

In order to generate an effective radiation therapy plan, the distortions of the magnetic fields are measured and evaluated to determine if there has been any change. Where the distortions change and a prior distortion correction is applied, the inaccuracies in the planning images are most pronounced towards the edges. Radiation therapy plans are dependent on the geometric accuracy of the MR images. The magnetic field distortion can be significantly changed by small metallic, particularly ferrous, parts such as paper clips, iron filings, coinage, screws, nails, etc. which can slip undetected into the magnet bore.

The present application provides a regular quality assurance process which provides RT planning assurance such that any MR images used in the RT planning process are within an acceptable tolerance. Typically, phantoms are used to determine the geometric accuracy of a MR image. Prior phantoms were often a 2D grid phantoms which were positioned and imaged in different planes, e.g. 3 orthogonal planes. The distortion mapping using a 2D phantom involves repeated imaging with physical movement of the phantom to represent possible imaging planes. The process of multiple images and repeated physical movement of the phantom use valuable clinical time and staff resources. In addition, 2D phantoms did not measure distortion spanning the entire 3D imaged volume, only the positions in which the 2D phantom is placed. The 3D phantoms employed for MR scanner calibration are very heavy, i.e. 45-90 kg (100-200 lbs.). Heavy phantoms are difficult to move physically, and often involve multiple persons and/or mechanical lifts to safely move the phantom into position. Due to the weight, such phantoms may not measure the entire field of view. Current industry standards call for manually lifted containers and packages to about 18 kg (40 lbs) or less. Lighter weights are more easily moved by an individual and are less likely to result in back or other injuries. There are currently no mandatory standards for quality assurance of MR images used in RT planning, but standards are expected to develop and are beneficial the RT planning process.

The following discloses a new and improved medical image phantom and quality assurance process for magnetic resonance imaging used in radiation planning which addresses the above referenced issues, and others.

In accordance with one aspect, a system for quality assurance of a magnetic resonance (MR) imaging device used in magnetic resonance based radiation therapy planning includes a phantom weighing less than 18.2 kg (40 lbs.). The phantom includes a three dimensional spatial distribution of MR and CT imagable elements located in an MR and CT inert foam support, and an MR and CT inert external support structure which surrounds and hermetically seals the foam support. The spatial distribution is sized to completely fill an imaging volume of the magnetic resonance imaging device.

In accordance with another aspect, a method of quality assurance using a phantom for radiation therapy planning includes manually lifting a medical imaging phantom which weighs less than 18.2 kg into a magnetic resonance (MR) imaging device. The medical imaging phantom includes a three dimensional spatial distribution of MR and CT imagable elements located in an MR and CT inert foam support, and an MR and CT inert external support structure which surrounds and hermetically seals the foam support. The spatial distribution is sized to completely fill an imaging volume of the magnetic resonance imaging device. An MR phantom image is acquired with the MR imaging device. The locations of the imagable elements from the MR phantom image are compared with locations of the imagable elements in a previously acquired CT reference image.

In accordance with another aspect, a medical imaging phantom weighing less than 18.2 kg (40 lbs.) includes a three dimensional spatial distribution of MR and CT imagable elements located in an MR and CT inert support, and an MR and CT inert external support structure which surrounds and hermetically seals the support. The spatial distribution is sized to completely fill an imaging volume of a magnetic resonance imaging device.

One advantage resides in a regular, e.g. daily, calibration.

Another advantage is a lightweight and durable phantom which spans a imaging volume in one imaging data acquisition.

Another advantage is the low cost, low weight, and high stability of a medical imaging phantom.

Another advantage resides in the ease of lifting and using the phantom on a daily basis by a single person.

Another advantage is that the medical imaging phantom does not require a high degree of accuracy to manufacture, but is highly accurate.

Another advantage is the detection of MR geometric distortions in a full MR imaging volume.

Another advantage is the quality assurance provided for MR based radiation therapy.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
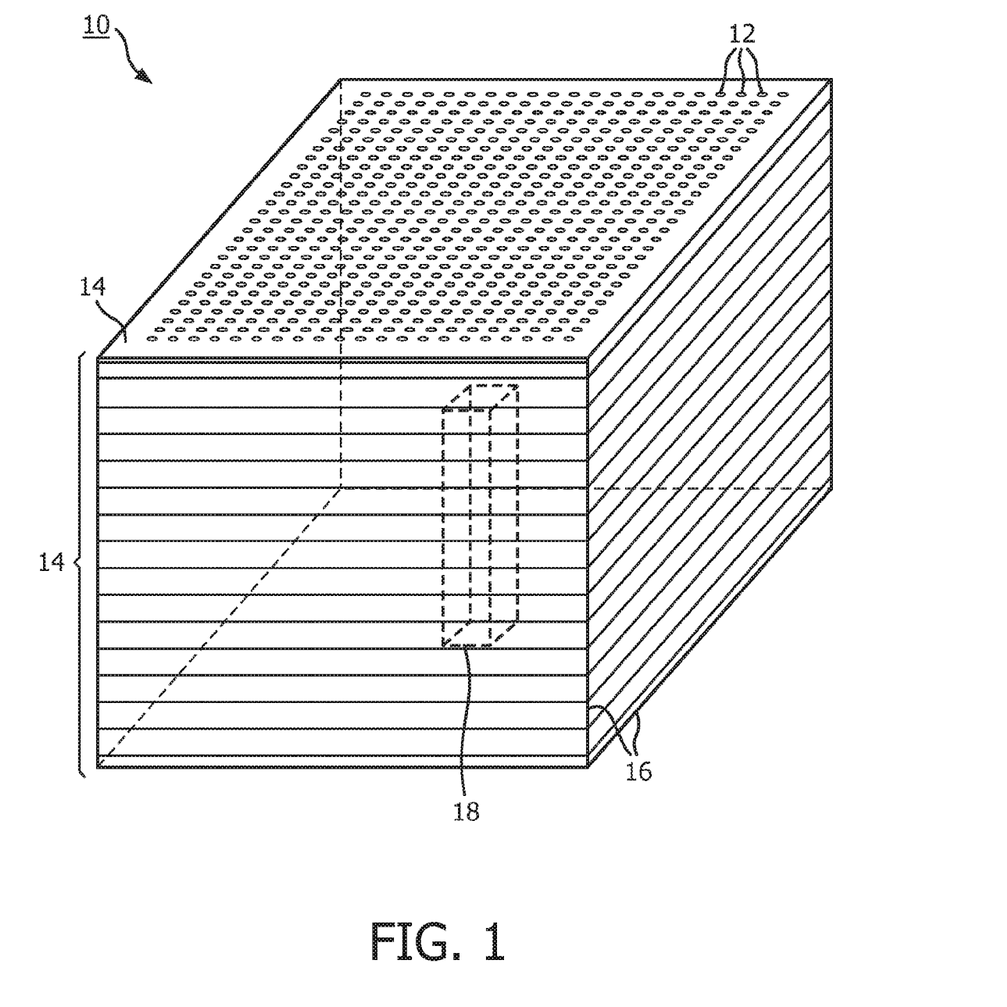
FIG. 1 schematically illustrates an embodiment of the medical imaging phantom.

With reference to FIG. 1, an embodiment of a medical imaging phantom 10 is shown. The medical imaging phantom 10 includes a three dimensional spatial distribution of magnetic resonance and CT imagable elements 12 in a magnetic resonance and CT inert foam support 14. The three dimensional spatial distribution can include lattices such as cubic lattices, hexagonal lattices, concentric spheres, concentric cylinders, radial grids, combinations, placement of the imagable elements on the null points and planes of spherical harmonic functions and the like. The active material of the imagable elements 12 is held in containers such as soft-gel capsules, which are inserted into wells in the support foam 14. In one embodiment, the imagable elements are placed in about 2.5 cm (1 inch) intervals in the x and y directions on sheets of foam. Sheets of foam, approximately 2.5 cm (1 inch) thick are stacked. The size of the intervals can be varied according to the spatial dimensions measured for distortions and the degree of quality to be assured. The sheets of foam ease manufacturing constraints. In one embodiment, the containers of the active material are oval shaped, but can be circular, cylindrical, or any regular shape, particularly shapes whose geometric center is easily calculated. One example includes sealed glass micro-bulbs of the type used in high resolution spectrometers. Another example is over the counter laxative or vitamin E soft-gel capsules. The amount of active material in each capsule is uniform, but can vary. Pharmaceutical standards are sufficient for the dosage such as a standard size 5 capsule. The tolerance of the spacing is about +/−0.0508 cm or greater. The tolerance can be large compared with the accuracy, because the accuracy is calibrated by a phantom reference image and not the phantom itself. The chosen spatial distribution of the imagable elements can help reduce the computational aspects of determining the actual position of the imagable elements in the MR phantom image. The larger tolerance also reduces the manufacturing complexity and cost.

The foam support 14 provides support to the imagable elements 12 while adding minimal weight. The size of the phantom 10 and the amount of foam and the foam weight to fill the phantom determine the phantom weight. The design provides a phantom less than about 18 kg (40 lbs.) and fills the MR imaging volume. The MR imaging volume spans the entire region in the bore of the MR imaging device where the MR gradient coils are designed to generate linear magnetic field gradients. The low weight permits easy loading and movement by a single individual. In one embodiment, the phantom measures 40 cm×40 cm×40 cm and weighs less than 9 kg. The size of the phantom is limited by the bore openings of the imaging devices which use the phantom. The shape of the phantom can be cubic, rectilinear, cylindrical, elliptically cylindrically, or approximate the shape of human anatomy. Foam such as polystyrene, polyethylene, polyvinylchloride (PVC), closed cell foam rubber or polyimide can be used which reduces the overall weight of the phantom. Other foam materials include non-plastic foam such as aerogel. The foam can be molded or cut to the necessary dimensions. Alternatives to foam can include paper, cardboard, balsa wood, and the like. The characteristics of the foam support include moisture proofing, strength, rigidity, wear resistance, low MR signal, and permeability to radio frequency waves.

The foam support 14 is surrounded by a magnetically inert external support structure 16, such as acrylic plastic sheets which is hermetically sealed. Other materials for the external support structure include polytetrafluoroethylene (e.g. Teflon), polyoxymethylene (e.g. Delrin), polycarbonate, nylon, fiberglass composite, plywood, etc. The external support structure 16 prevents damage to the foam and shifting of the imagable elements and enhances durability and stability of the phantom. Optionally, a desiccant can be sealed inside the phantom. Other optional features include feet attached to the base of the phantom to level the phantom after loading in the imaging device. Another optional feature is the inclusion of levelers in two directions such as bubble levels. The levelers can be relative to the support structure or a reference column 18. Another optional feature are guidelines recessed on the outside of the phantom. The guidelines can be used to align the phantom to an external laser bridge system commonly used to align patient marking in RT.

Within the foam support 14 is the reference column 18, such as an acrylic plastic circular or rectilinear tube filled with a material visible to CT and MR imaging devices such as water. The column 18 can be located in a position between any two walls of the external support structure. The column 18 provides a spatial reference and reduces the computational aspects of locating the imagable elements 12. The material in the reference column provides a strong signal reference to a central magnetic resonance frequency and for radio frequency power calibration. The reference column also provides a geometric reference in the image planes. The material in the reference column can be the same as the imagable elements or different.

Figure 2A:
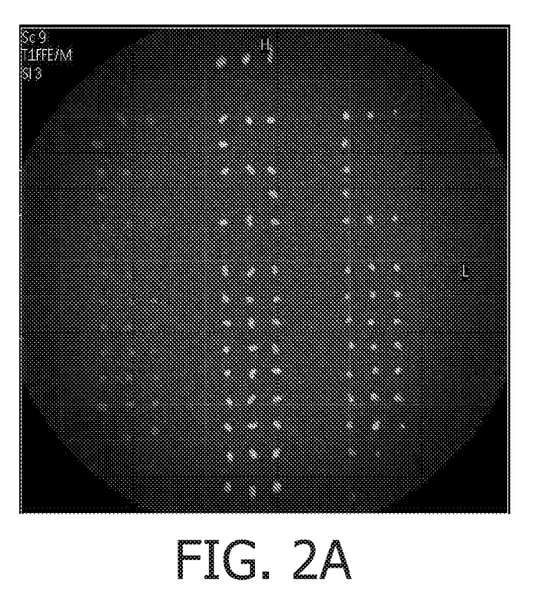
FIGS. 2A-B illustrates various regularly spaced materials tested in the phantom to measure the spatial distortions.
Figure 2B:
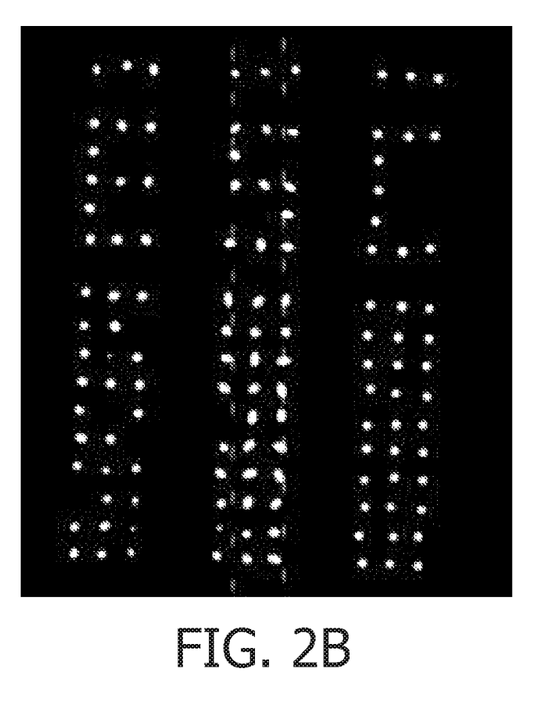

In FIGS. 2A-2B, various imagable elements used in the phantom to measure the spatial distortions are shown in a study. FIG. 2A shows an MR image of three different materials while FIG. 2B shows a corresponding CT image of the same materials. The images are of a polystyrene tray with a section of vitamin E soft-gel capsules (i.e. E section), sodium docusate soft-gel capsules (i.e. S section), and calcium docusate soft-gel capsules (i.e. C section). In the MR image, the E section is barely visible while the brightest image is from the S section, followed by the C section. All sections are fairly visible in the CT image, particularly the S section or sodium docusate. The active material of the imagable elements include commercially available materials at a low cost such as fish oil. A property of the active material includes contrast in both the CT and MR image.

Figure 3:
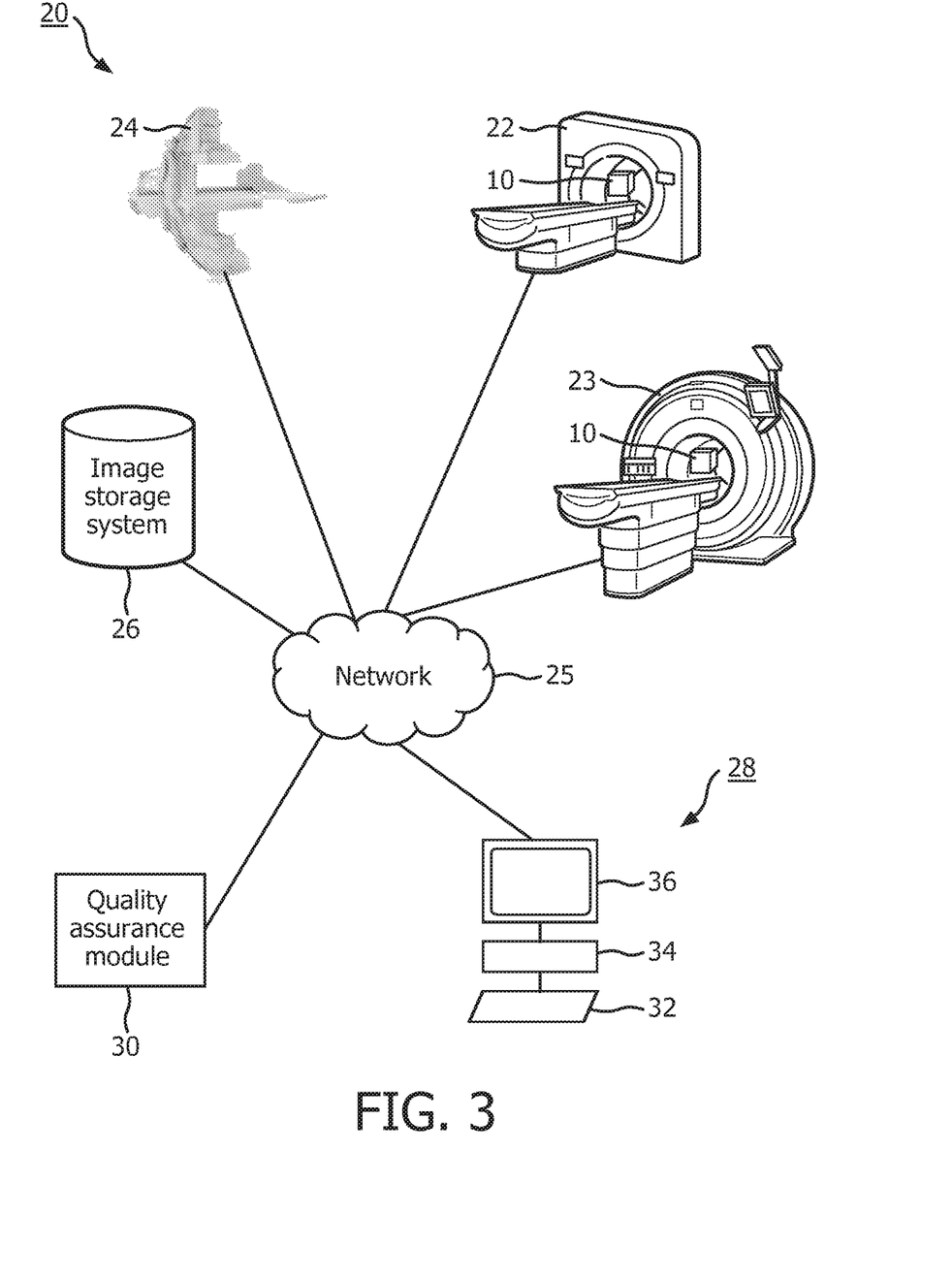
FIG. 3 schematically illustrates one embodiment of the quality assurance system.

FIG. 3 schematically illustrates one embodiment of the quality assurance system 20. The system 20 includes an x-ray computed tomography (CT) medical imaging device 22, a magnetic resonance (MR) imaging device 23, and a radiation treatment device 24. The imaging devices can be combinations devices or separate devices. Combination devices are typically inherently registered while separate devices require a registration step. Initially, the phantom 10 is loaded into the bore of the CT imaging device 22 for a full volume image or map filled by the entire phantom 10. The CT medical imaging device 22 can be at a manufacturing site or can be connected to a network 25 at a medical site which transmits the image and other data. The CT imaging device generates a phantom reference image which shows the actual locations of imagable element 12. The CT phantom reference image or a map of the geometric centers of the elements 12 based thereon is unique to the calibrated phantom. The phantom and the CT image have unique identifiers that identify them as a corresponding pair. If the CT phantom image is generated remotely, it can be stored on a computer readable storage medium which is shipped with the phantom.

For daily calibration of the MR imaging device 23, the phantom 10 is loaded into the MR imaging device and accurately positioned in the field of view. The MR imaging device generates a quality assurance image. The phantom reference image and/or quality assurance image are stored in a data store. The data store can be in local memory, disk, or in a storage management system 26 such as a Picture Archiving and Communication System (PACS), a Radiology Information System (RIS), and the like.

A workstation 28 connects to the network 25 and a healthcare practitioner activates the quality assurance module 30 using at least one input device 32. The workstation 28 includes an electronic processor or electronic processing device 34, a display 36 device which displays the phantom reference image, quality assurance image, and/or quality assurance results, menus, panels, and user controls, and the at least one input device 32 which inputs the healthcare practitioner selections. The workstation 28 can be a desktop computer, a laptop, a tablet, a mobile computing device, a smartphone, and the like. The input device 32 can be a keyboard, a mouse, a microphone, touch screen, and the like. The display device includes one or more of a LCD display, an LED display, a plasma display, a projection display, a touch screen display, and the like.

The quality assurance module 30 is suitably embodied by an electronic data processing device, such as the electronic processor or electronic processing device 32 of the workstation 28, or by a network-based server computer operatively connected with the workstation 28 by the network 25, or so forth. Moreover, the disclosed phantom imaging and comparison are suitably implemented as a non-transitory storage medium storing instructions (e.g., software) readable by an electronic data processing device and executable by the electronic data processing device to perform the disclosed quality assurance techniques.

The quality assurance module 30 manages and performs the process of quality assurance of the MR imaging device for radiation therapy planning. The process of quality assurance includes the imaging of the phantom by the CT and MR imaging devices, comparison of the phantom images, and the reporting of the results of the quality assurance process. The quality assurance module includes tracking the use of the phantom, the generated phantom reference image, the identification of the phantom, the generated phantom quality assurance image, the currency of the images, how the images are compared, and the amount of distortion of the quality assurance image based on the reference image. Results are displayed to the healthcare practitioner through the display device. Results can include recommendations of success or failure, any remedial actions and/or related informational items.

Figure 4:
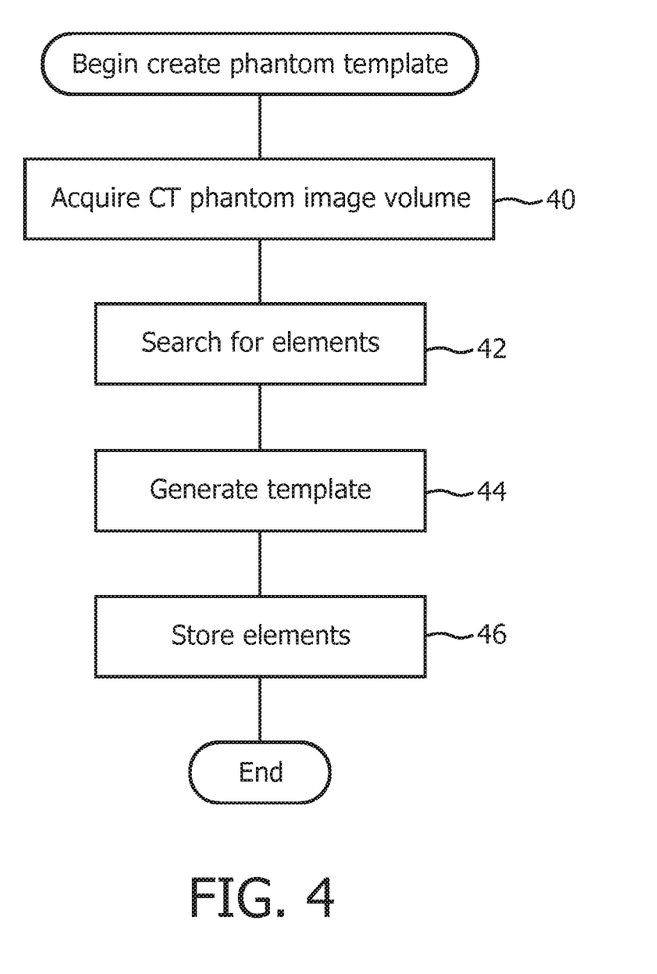
FIG. 4 flowcharts an embodiment of a phantom calibration.

With reference to FIG. 4, an embodiment of the phantom reference image or template creation is flowcharted. In a step 40, a CT imaging device is initiated and a CT image of the phantom is acquired. The phantom reference image is a 3D volume image of the elements 12. A template is generated from the phantom reference image in the following steps.

In a step 42, the 3D CT image is searched to locate the elements 12. The reference column 18 and the a priori known expected intervals and tolerances provide references which reduce the computational aspects of finding the actual positions of the imagable elements. Each element is located based on the contrast of the CT image, and any a priori information available. The search can be performed as a coarse segmentation or estimate of the elements using a geometric shape such as a cube.

A template is generated in a step 44. The centers of each imagable element are identified using a centering function such as a center of mass and represented in spatial coordinates. The centering function minimizes the error associated with variability of the size and placement of each regularly spaced material. For example, a soft-gel capsule will vary within certain tolerances both in material and in size. By using the center instead of the edges the reference location is more easily identified and associated with other reference locations.

The template of the centers of the elements 12, and/or the CT phantom reference image are stored in a step 46. The phantom reference image and/or template can be stored in the storage management system 26. The template can include the phantom identification either obtained from the phantom reference image and/or manual entry.

Figure 5:
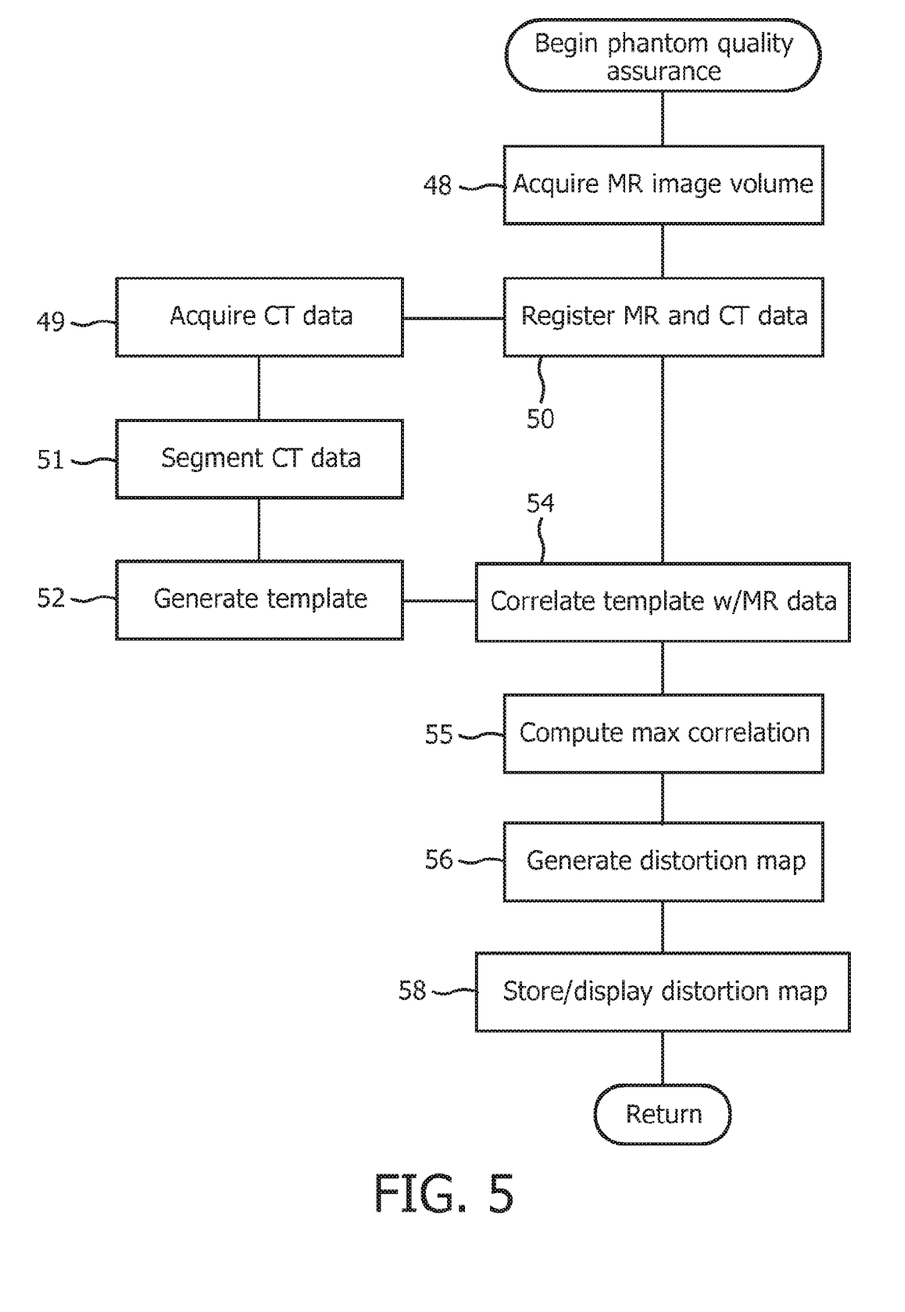
FIG. 5 flowcharts an embodiment of a magnetic resonance phantom quality assurance.

With reference to FIG. 5, an embodiment of the phantom quality assurance for the MR imaging device is flowcharted. In a step 48, the phantom is accurately positioned in the field of view and the MR imaging device is initiated to acquire the MR phantom quality assurance image. The reference column such as an internal tube filled with material can optionally provide a reference to the acquisition process. Optionally, in the step 48, the signal from the center tube is used to perform a central frequency calibration and/or an RF power calibration. In a step 49, the CT phantom reference image is acquired, and in a step 50, the CT phantom reference image and MR quality assurance image are registered.

The CT phantom reference image is segmented in a step 51. The CT image is segmented into unit cells based on the phantom design specifications and registration markers. Each unit cell contains one imagable element. In a step 52, the template is generated from the segmented unit cells.

In a step 54, a search is performed for the imagable elements in the MR image by correlating the location of each template location with the associated unit cells in the MR QA image. The three dimensional ordered distribution of elements are contrasted in the MR image. Each imagable element is located. The reference column and other a priori information about the spatial distribution reduce the computational aspects of locating the imagable elements. The center of each imagable element is computed and compared with the coordinate of the corresponding template or CT phantom reference image element. For example, the center of each element in the template is represented in Cartesian coordinates as (x,y,z). The corresponding coordinates of the element, $(\bar{x},\bar{y},\bar{z})$, in the MR image can be represented as $\bar{v}=v+\eta_v$, (v) where v is any one of the spatial dimensions (x,y,z) and $\eta_v$, represents the induced distortion and is given by $$\eta_v(x, y, z) = \frac{B_v^N(r, \theta, \phi)}{G_v^L},$$

where $B_v^N$ is the non-linear magnetic field due to the v gradient channel expressed in spherical harmonics as:

$$B_v^N(r,\theta,\phi)=B_{x(1,0)}(r,\theta,\phi)+\Sigma_{n=2}\Sigma_m B_{x(n,m)}(r,\theta,\phi) \text{ and}$$

$$B_{x(n,m)}(r,\theta,\phi)=r^n[a_{v(n,m)}\cos(m\phi)+b_{v(n,m)}\sin(m\phi)]P_{(n,m)}(\cos \theta)$$

where (r, θ, ϕ) are spherical coordinates. Here, $a_{v(n,m)}$ and $b_{v(n,m)}$ are spherical harmonic co-efficients of degree n and order m. Similarly, $P_{(n,m)}$ is the associated Legendre polynomial of degree n and order m. $G_v^L$ is the linear part of the v gradient channel and is given by $G_x^L=a_{x(1,1)}$, $G_y^L=b_{y(1,1)}$, $G_z^L=a_{z(1,0)}$. A maximum correlation is computed which provides the shift or distortion in 3 dimensions in a step 55.

Using the computed difference between each center of the element in the MR image and the center of the element in the template or CT phantom reference image, a distortion map is generated in a step 56. The distortion map includes the differences in the centers between the CT phantom reference or template and the MR image. The distortion map can interpolate for all points in the field of view. In a step 58, the distortion map is stored.

Figure 6:
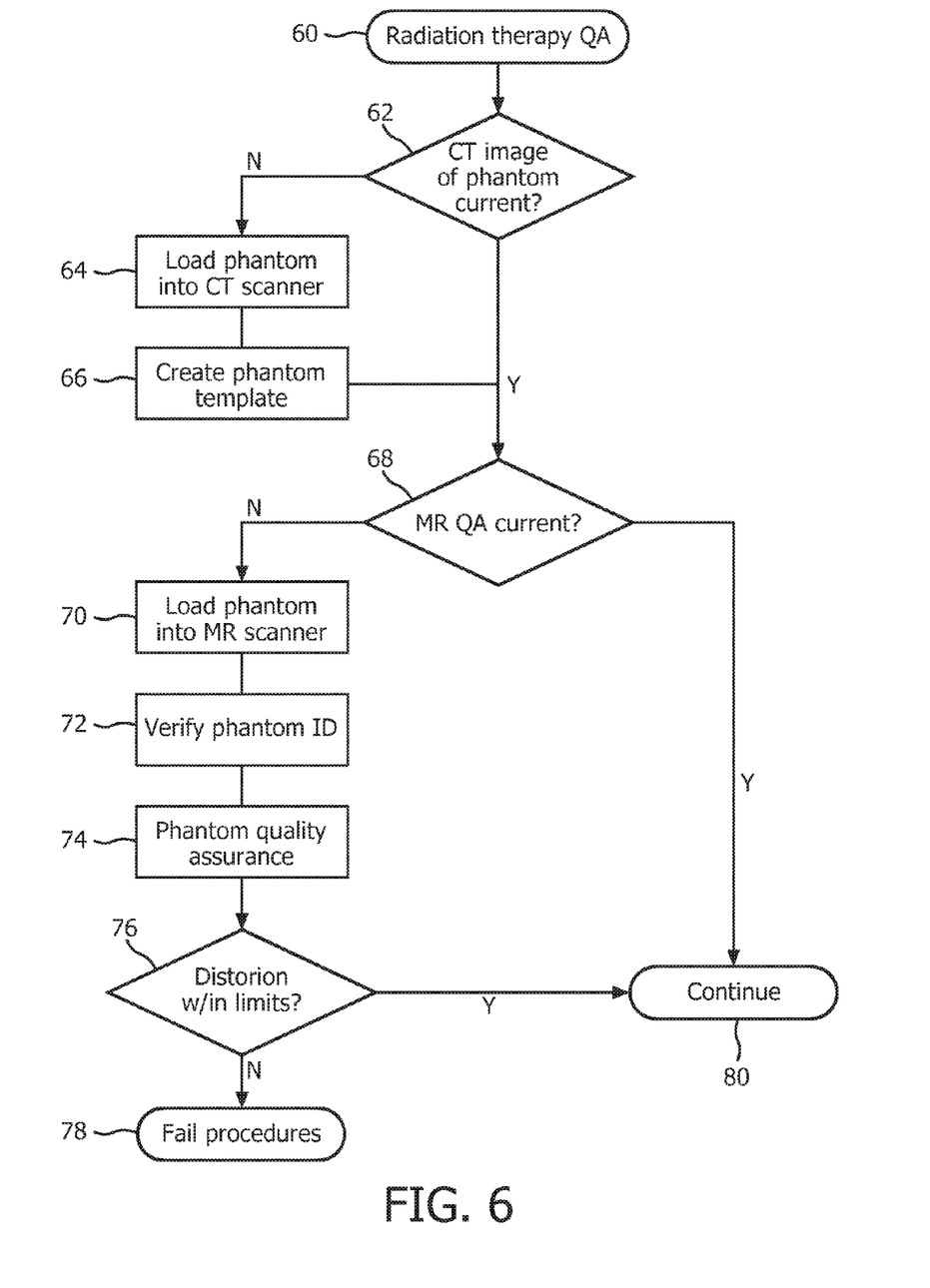
FIG. 6 flowcharts an embodiment of radiation therapy quality assurance.

An embodiment of the quality assurance (QA) of MR for radiation therapy planning is flowcharted in FIG. 6. The QA method includes both steps performed by the healthcare practitioner, those performed by a medical imaging device and/or quality assurance module, and those performed by the healthcare practitioner and guided by the quality assurance module. The quality assurance module guides the overall process beginning in a step 60.

The quality assurance module verifies the currency of the CT phantom reference map in a step 62. Verifying the currency of the CT phantom includes comparing the date of any stored phantom reference image with the current date and the expected interval based and the recommended standard. For example, if the CT phantom reference image is expected to be updated whenever the phantom is new and/or replaced, or annually, then a new phantom reference image is acquired if the image data is older than one year or if the phantom identification has changed. The phantom identification can be a physical label on the phantom and can also be a label which is contrasted in the image. The identification can be written and/or encoded such as a barcode.

If a new phantom reference image is to be created, then the quality assurance module can direct the healthcare practitioner to load the phantom into the CT imaging device in a step 64. The phantom is loaded in the imaging area or field of view of the CT imaging device such that a full volume CT image is filled by the phantom. Optional levelers and feet on the phantom aid the healthcare practitioner in the placement and orientation of the phantom in the imaging device. The quality assurance module can optionally demonstrate the process with a short video displayed with the display device or simply provide written instructions. The CT phantom reference map is created in a step 66 and as described with reference to FIG. 4.

The currency of the MR QA is checked in a step 68. The currency of the MR QA includes a different periodicity than the CT phantom reference image such as daily. The quality assurance module can optionally verify the schedule for MR RT planning images and modify the periodicity. For example, if no MR RT planning images are scheduled for the day or if a MR QA image has already been acquired based on a MR QA image date, then a MR QA image acquisition is unnecessary.

If a new MR QA image is indicated, then the phantom is loaded into the MR imaging device in a step 70 by the healthcare practitioner. The phantom is placed in the bore of the imaging device such that the imaging volume is filled by the phantom. The placement and orientation of the phantom in the imaging device include the step 64 the same as or similar to the loading of the phantom in the CT imaging device. If the devices are a hybrid device and share a common field of view, then the loading is the same. If the devices are separate, then the loading is similar.

In a step 72, the phantom identifier is verified. Verification can include visual identification by the healthcare practitioner, entry of an identifier code into the system via the user input device, use of a label included in the phantom quality assurance image, and the like.

The phantom QA is performed in a step 74 as described in reference to FIG. 5. The step returns a distortion map. The distortion map includes the computed differences between the CT phantom reference image or template and the MR phantom image or MR QA image. The distortion map represents changes in the spatial coordinates of the MR device which can occur in a MR RT image.

The distortion map is checked in a step 76. Threshold values are employed to determine if the distortions are within acceptable levels for quality assurance. The distortion map can be displayed via the display device as graphical images and/or statistical graphs and/or numeric representations such as mean, variance, maximum variance, mean variance, and the like. The magnitude of the distortions or degree of shift can be displayed using color contrasts. Visualizations of the distortions are facilitated in any arbitrary plane by the interpolation included in the distortion map. The display plane can be extracted from a 3D matrix resulting from the interpolated distortion map.

If distortions are not within acceptable levels, then the system provides notice in a step 78. Notice can include display of a message on the display device 36. Notice can include recording statistics or other information regarding the measured distortions for future analysis. Notice can also include display of the distortion map. The step can provide iterative corrections and return to earlier steps to determine whether corrections are effective. If distortions are within or have been brought within acceptable levels, then notification occurs in a step 80.

If the centers match within a predefined tolerance, a calibration successful message is generated on the display 36 in a step 80. The calibration successful message can include display of the distortion map and/or other statistics relevant to radiation therapy planning.

The generated distortion map can also be generated by comparing a user acquired CT image of the phantom with the stored CT reference image of the phantom, which provides a quality check on the mechanical integrity of the phantom. The distortion maps can also be compared over time such as over the course of a patient's treatment. For example, a statistic such as a minimum, mean, maximum can be plotted to compute the differences in distortion values for each imagable element.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A phantom for quality assurance of a magnetic resonance (MR) imaging device, comprising:
    a known three dimensional spatial distribution of MR and computer tomography (CT) imageable elements located in an MR and CT inert foam support, the spatial distribution being sized to completely fill an imaging volume of the magnetic resonance imaging device;
    a reference column; and
    an MR and CT inert external support structure, which surrounds and hermetically seals the foam support, wherein the phantom weighs less than 18.2 kg (40 lbs.).

2. The phantom according to claim 1, wherein the reference column is filled with material which provides at least one of:
    a strong signal reference to a central magnetic resonance frequency;
    a strong signal reference for radio frequency power calibration; and
    a geometric reference in image planes.

3. The phantom according to claim 1, wherein the phantom spans at least 40 cm in each of three spatial dimensions.

4. The phantom according to claim 1, further including at least one of:
    a desiccant sealed inside the phantom;
    feet attached to the base of the phantom configured for leveling the phantom;
    levels in two directions configured to indicate the level of the phantom; and
    guidelines recessed on the outside of the phantom.

5. A system for quality assurance of a magnetic resonance (MR) imaging device, comprising:
    a phantom, the phantom weighing less than 18.2 kg (40 lbs.) and including a known three dimensional spatial distribution of MR, and computer tomography (CT) imageable elements located in an MR and CT inert foam support, the spatial distribution being sized to completely fill an imaging volume of the magnetic resonance imaging device,
    a reference column filled with a material which provides a reference signal at a central magnetic resonance frequency, and
    an MR and CT inert external support structure, which surrounds and hermetically seals the foam support; and
    one or more processors configured to:
        acquire an MR image of the phantom with the MR imaging device,
        identify locations of the imageable elements in the MR phantom image, and
        compare the locations of the imageable elements from the MR phantom image with locations of the imagable elements in a previously acquired CT reference image.

6. The phantom according to claim 5, wherein the one or more processors are further configured to:
    acquire the CT reference image of the phantom from a CT imaging device;
    register the CT reference image and the MR image;
    segment the CT image into unit cells based on the spatial distribution of imageable elements such that each imageable element is in one unit cell;
    generate a template which includes the location of each imagable element;
    correlate the location of each imageable element in the template with an associated volume in the MR image;
    compute the maximum correlation; and
    generate a distortion map based on the maximum correlation.

7. The system according to claim 2, further including:
    a non-transitory computer readable medium storage carrying at least one of the CT phantom image or the MR phantom image.

8. A method of quality assurance using a phantom for radiation therapy planning, comprising:
    manually lifting a medical imaging phantom which weighs less than 18.2 kg into a magnetic resonance (MR) imaging device, and the medical imaging phantom including:
        a known three dimensional spatial distribution of MR and computed tomography (CT) imageable elements located in an MR and CT inert foam support, the spatial distribution being sized to completely fill an imaging volume of the magnetic resonance imaging device;
        a reference column including a material configured to resonate at a reference frequency; and an MR and CT inert external support structure which surrounds and hermetically seals the foam support;

acquiring an MR phantom image with the MR imaging device, the MR phantom image depicting the MR imageable elements and the reference column.

9. The method according to claim 8, further including:
acquiring a CT reference image of the phantom from a CT imaging device;
registering the CT reference image and the MR phantom image;
segmenting the CT reference image into unit cells based on the spatial distribution of imageable elements such that each imageable element is in one unit cell;
generating a template which includes the location of each imageable element;
correlating the location of each imageable element in the template with an associated volume in the MR phantom image;
computing a maximum correlation; and
generating a distortion map based on the maximum correlation.

10. The method according to claim 9, further including:
repeating generating the distortion maps over time; and
comparing the distortion maps.

11. The method according to claim 8, further including:
calculating centers of each imageable element in MR coordinates $(\bar{x},\bar{y},\bar{z})$ using CT coordinates $(x,y,z)$, represented as $\bar{v}=v+\eta_v(x, y, z)$ where $v$ is any one of the spatial dimensions $(x,y,z)$, and $\eta_v$ represents the induced distortion and is given $$\eta_v(x, y, z) = \frac{B_v^N(r, \theta, \phi)}{G_v^L},$$

by where $B_v^N$ is the non-linear magnetic field due to the $v$ gradient channel expressed in spherical harmonics as:

$$B_v^N(r,\theta,\phi)=B_{x(1,0)}(r,\theta,\phi)+\Sigma_{n=2}\Sigma_m B_{x(n,m)}(r,\theta,\phi) \text{ and}$$

$$B_{x(n,m)}(r,\theta,\phi)=r^n[a_{v(n,m)}\cos(m\phi)+b_{v(n,m)}\sin(m\phi)]P_{(n,m)}(\cos \theta)$$

where $(r,\theta,\phi)$ are spherical coordinates, $a_{v(n,m)}$ and $b_{v(n,m)}$ are spherical harmonic co-efficients of degree n and order m, and $P_{(n,m)}$ is the associated Legendre polynomial of degree n and order m.

12. The method according to claim 8, further including:
verifying the MR phantom image is the same as the phantom of the CT image based on an identity of the phantom; and
displaying on the display device a message that calibration is successful.

13. The method according to claim 10, wherein the reference column is used to perform at least one of:
identifying a signal reference to a central magnetic resonance frequency;
identifying a signal reference for radio frequency power calibration; and
identifying a geometric reference in image planes.

14. The method according to claim 8, further including:
comparing locations of the imageable elements from the MR phantom image with locations of the imageable elements in a previously acquired CT reference image; and
comparing the reference frequency to a target central magnetic resonance frequency of the MR imaging device.

15. A system comprising:
a magnetic resonance (MR) imaging device having an imaging volume of the MR imaging device, the MR imaging device being configured to generate MR images of objects disposed in the imaging volume; and
a phantom for quality assurance of the magnetic resonance (MR) imaging device, the phantom weighing less than 18.2 kg (40 lbs.), and including:
a three dimensional spatial distribution of MR and computer tomography (CT) imageable elements located in an MR and CT inert foam support, the spatial distribution being sized to completely fill the imaging volume;
a reference column for spatial referencing of the imageable elements, the reference column being filled with material configured to provide a signal reference at a central magnetic resonance frequency of the MR imaging device, and
an MR and CT inert external support structure which surrounds and hermetically seals the foam support.

16. The system according to claim 15, wherein the foam support includes at least one of:
polystyrene;
polypropylene;
polyvinylchloride (PVC);
closed cell foam rubber;
aerogel;
paper;
cardboard;
balsa wood;
polyethylene; and
polyimide.

17. The system according to claim 15, wherein the external support structure includes at least one of:
acrylic plastic;
polytetrafluoroethylene;
polyoxymethylene;
polycarbonate;
polythene;
polypropylene;
nylon;
fiberglass composite; and
plywood.

18. The system according to claim 15, further including:
one or more processors configured to:
acquire an MR image of the phantom with the MR imaging device;
identify locations of the imageable elements in the MR phantom image;
compare the locations of the imageable elements from the MR phantom image with locations of the imageable elements in a previously acquired CT reference image.

* * * * *